United States Patent [19]

Suzuki et al.

[11] Patent Number: 4,994,254

[45] Date of Patent: Feb. 19, 1991

[54] ALUMINOGALLOSILICATES OF THE MFI TYPE

[75] Inventors: Isao Suzuki; Kazuo Hirabayashi, both of Yokohama, Japan

[73] Assignee: Research Association For Utilization Of Light Oil, Japan

[21] Appl. No.: 322,988

[22] Filed: Mar. 14, 1989

Related U.S. Application Data

[60] Division of Ser. No. 163,188, Feb. 25, 1988, Pat. No. 4,861,934, which is a continuation-in-part of Ser. No. 1,370, Jan. 8, 1987, abandoned.

[51] Int. Cl.$^5$ .............................................. C01B 33/28
[52] U.S. Cl. .................................... 423/328; 423/329; 502/77
[58] Field of Search ..................... 423/328, 329, 330; 502/60, 61, 62, 77

[56] References Cited

U.S. PATENT DOCUMENTS

| | | | |
|---|---|---|---|
| 3,709,979 | 1/1973 | Chu | 423/328 |
| 3,832,449 | 8/1974 | Rosinski et al. | 423/328 |
| 4,208,305 | 6/1980 | Kouwenhoven et al. | 423/328 |
| 4,372,930 | 2/1983 | Short et al. | 423/328 |
| 4,420,467 | 12/1983 | Whittam | 423/328 |
| 4,510,256 | 4/1985 | Zones | 423/328 |
| 4,528,171 | 7/1985 | Casci et al. | 423/328 |
| 4,537,754 | 8/1985 | Casci et al. | 423/328 |
| 4,581,211 | 4/1986 | Araga et al. | 423/328 |
| 4,581,212 | 4/1986 | Araga et al. | 423/328 |
| 4,610,854 | 9/1986 | Zones | 423/328 |
| 4,705,674 | 11/1987 | Araga et al. | 423/328 |
| 4,743,437 | 5/1988 | Whittan | 423/328 |
| 4,826,667 | 5/1989 | Zones et al. | 423/328 |
| 4,834,958 | 5/1989 | Zones | 423/328 |
| 4,836,996 | 6/1989 | Casci et al. | 423/328 |

FOREIGN PATENT DOCUMENTS 84-03879 10/1984 World Int. Prop. O. .......... 423/328

Primary Examiner—John Doll
Assistant Examiner—R. Bruce Breneman
Attorney, Agent, or Firm—Lorusso & Loud

[57] ABSTRACT

A high-octane gasoline is produced by the conversion of a light hydrocarbon containing $C_2$–$C_7$ paraffins and/or $C_2$–$C_7$ olefins using a crystalline aluminogallosilicate catalyst of the formula:

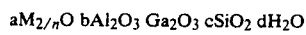

$$aM_{2/n}O \ bAl_2O_3 \ Ga_2O_3 \ cSiO_2 \ dH_2O$$

wherein M is a metal selected from an alkali metal, an alkaline earth metal and a mixture thereof, n is the valence of said metal, a is a positive number of $(b+1)\pm 3.0$, b is between 1 and 6, c is between 80 and 490, d is between 1 and 200, $c/(b+1)$ is between 40 and 70, and $c/b$ is between 46.7–140.

2 Claims, 8 Drawing Sheets

ALUMINOGALLOSILICATES OF THE MFI TYPE

This is a division of application Ser. No. 07/163,188 filed Feb. 25, 1988 now U.S. Pat. No. 4,861,934, filed of Ser. No. 07/001,370 filed Jan. 8, 1987 and now abandoned.

The present invention relates to a novel crystalline aluminogallosilicate and to a process for the preparation of a high-octane gasoline blending stock containing an aromatic hydrocarbon as a major constituent, which uses the crystalline aluminogallosilicate as a catalyst.

Heretofore, the catalytic reforming of naphtha using a platinum aluminium catalyst is extensively employed for the preparation of a high-octane gasoline. Naphtha to be used as a raw material is usually from fractions having boiling points in the range from 70° C. to 180° C., when intended to be used for the preparation of gasoline for use with automobiles and from fractions having boiling points in the range from 60° C. to 150° C., when intended to be used for the preparation of BTX. Accordingly, it is difficult to produce a high-octane gasoline from a light hydrocarbon containing a paraffin and/or an olefin having each carbon atoms ranging from 2 to 7 because a rate for the conversion to aromatic hydrocarbons may be decreased to remarkably low levels as the number of carbon atoms is decreased. At the present time, light hydrocarbons are used in very limited ranges as raw materials in the field of petrochemistry and for the preparation of city gases. Therefore, a technology designed to be applied to produce high-octane gasolines from light hydrocarbons draws high attention in terms of an increase in an addition to a value of light hydrocarbons and an increase in gasoline consumption.

As techniques relating to the preparation of high-octane gasoline blending stock are known various processes which involve, for example, the catalysis with a crystalline silicate, particularly the ZSM-5 silicate and those of the ZSM-5 type. Japanese Patent Early Publication No. 98,020/1984 discloses a process which comprises converting each of n-butane and propane to aromatic compounds by using a calcined product of a crystalline gallium silicate from a gel having the composition represented by the following formula:

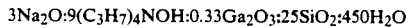

$$3Na_2O:9(C_3H_7)_4NOH:0.33Ga_2O_3:25SiO_2:450H_2O$$

as a catalyst after the ammonium ion exchange and calcination. These conventional processes, however, are not yet satisfactory from the industrial point of view because the yield of the high-octane gasoline from light hydrocarbons is low.

In accordance with the present invention, there is provided a process for the preparation of a high-octane gasoline, which comprises contacting a light hydrocarbon containing one or more paraffins and/or olefins, each having 2 to 7 carbon atoms with a crystalline silicate catalyst characterized in that said catalyst comprises an aluminogallosilicate with its skeleton comprised of $SiO_4$, $AlO_4$ and $GaO_4$ tetrahedra, and in that said contacting is performed at a temperature of 350°–650° C. under a hydrogen partial pressure of not higher than 5 kg/cm².

In another aspect, the present invention provides a crystalline aluminogallosilicate having the skeleton comprised of $SiO_4$, $AlO_4$ and $GaO_4$ tetrahedra and having the following formula:

$$aM_{2/n}O.bAl_2O_3.Ga_2O_3.cSiO_2.dH_2O$$

wherein M is a metal selected from an alkali metal, an alkaline earth metal and a mixture thereof, n is the valence of said metal, a is a positive number of (b+1)±3.0, b is between 0.3 and 30, c is between 8 and 2,000 and d is between 1 and 200.

The present invention will be described more in detail by referring to the drawings appended hereto. In the drawings, FIG. 1 is a graph showing the relationships of $SiO_2/T_2O_3$ (T: Al or Ga) vs. conversion and aromatics yield of an aluminosilicate and a gallosilicate for comparison uses;

Figure 6:
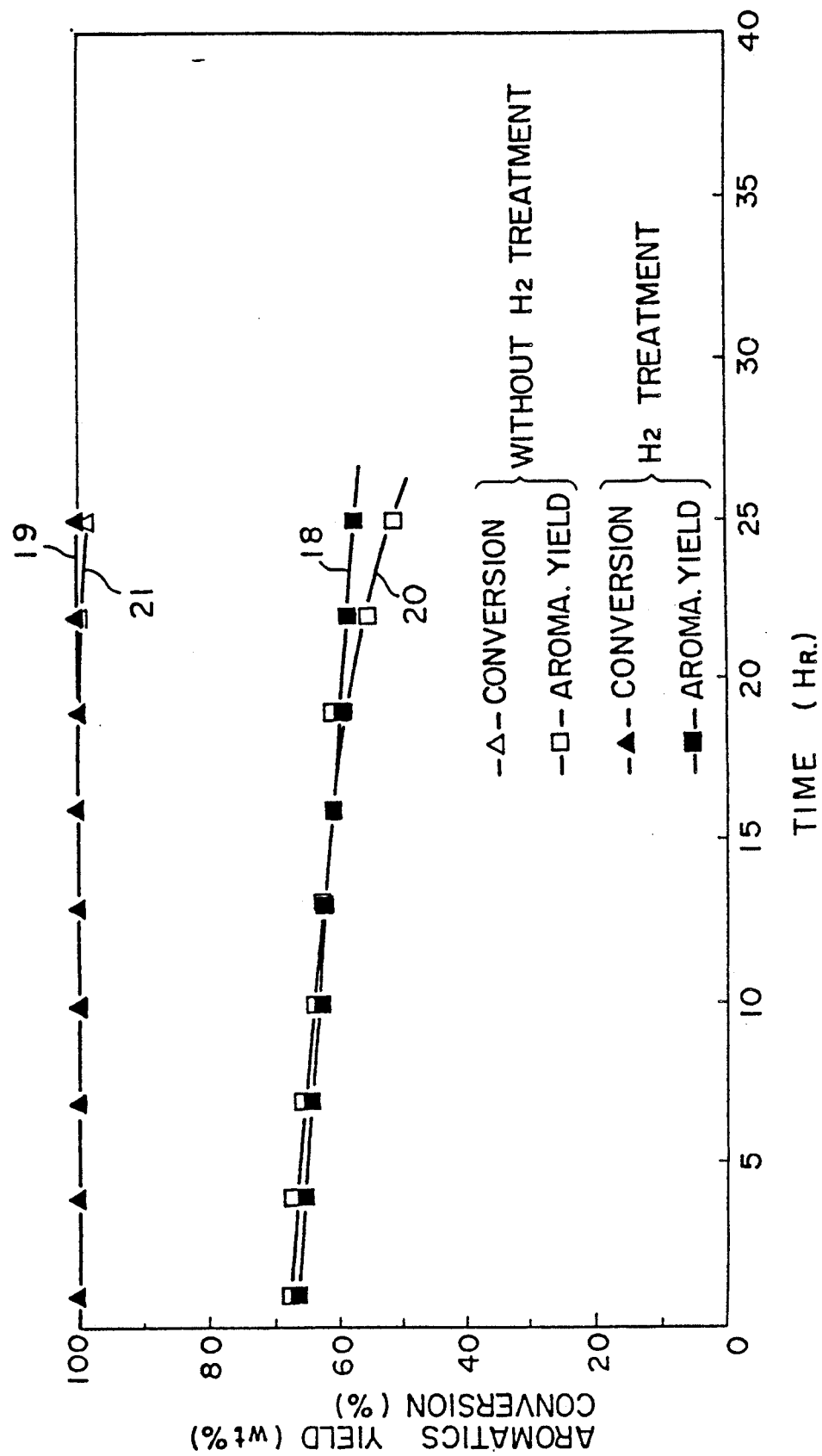
Figure 7:
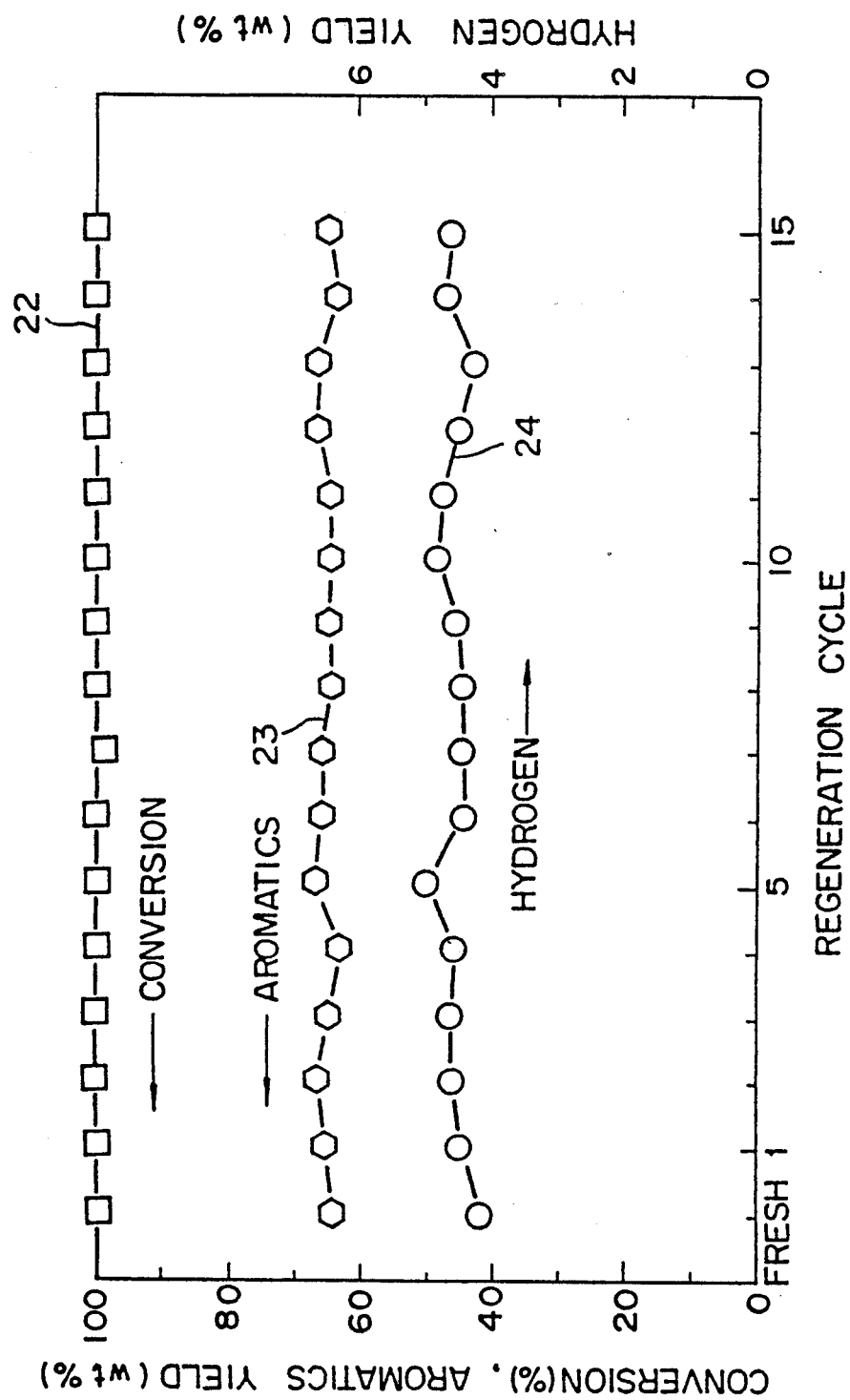

FIG. 6 is a graph showing the relationships of times vs. conversion and aromatics yields of the $H_2$-treated and untreated aluminogallosilcates according to the present invention; and FIG. 7 is a graph showing the relationships of regeneration cycles vs. conversion, aromatics yields and hydrogen yields of the aluminogallosilicate according to the present invention during the repetition of the reaction and regeneration cycles.

The terms "high-octane gasoline blending stock" and related ones referred to in the present specification mean hydrocarbons having the octane number of 95 or higher, when determined by the research method, and containing a large quantity of aromatic hydrocarbons with carbon atoms in the range from 6 to 10. The high-octane gasoline may be used as automobile fuel and for the preparation of aromatic hydrocarbons. The term "light hydrocarbons" referred to herein as raw materials for the preparation of high-octane gasoline means hydrocarbons containing a paraffin and/or an olefin with carbon atoms ranging from 2 to 7 as a major constituent. Representative of light hydrocarbons are light fractions having boiling points of 100° C. or lower obtainable from naphtha fractions containing a paraffin of carbon atoms ranging from 5 to 7 as a major constituent.

The crystalline aluminogallosilicate according to the present invention may be produced by the gel crystallization method using the hydrothermal synthesis or by the method of inserting gallium into the lattice skeleton of an aluminosilicate or a zeolite crystal.

The gel crystallization method is a simplified one because an objective quantity of aluminium and gallium can be contained at the same time in the preparation of a crystalline aluminogallosilicate. The crystalline aluminogallosilicate obtainable by the gel crystallization method may be produced by causing an aqueous mixture containing an alumina source and a gallia source as an essential constituent, in addition to a constituent necessary for the silicate synthesis, to be retained under conditions for the hydrothermal synthesis.

As sources of silica may be used, for example, a silicate such as sodium silicate, potassium silicate or the like, colloidal silica, silica powder, dissolved silica, soluble glass and so on. As sources of alumina are used, for example, an aluminium salt such as aluminium sulfate, aluminium nitrate or the like, an aluminate such as sodium aluminate, alumina gel and so on. As sources of gallia are used, for example, a gallium salt such as gallium nitrate, gallium chloride or the like, gallium oxide and so on. As a source of alumina or gallia, there may be used a solution or a hydroxide containing aluminium or gallium obtainable during the extraction or purification step of a deposit such as a bauxite deposit, zinc deposit or the like. An organic additive may also be used in order to accelerate the growth of a desired crystalline aluminogallosilicate and improve the purity thereof, thus yielding products of better quality. The organic additive to be used here may include, for example, a quaternary ammonium salt such as a tetrapropylammonium salt, a tetrabutylammonium salt, a tetrabutylammonium slat, a tripropylmethylammonium salt or the like, an amine such as propylamine, butylamine, aniline, dipropylamine, dibutylamine, morpholine or the like, an aminoalcohol such as ethanolamine, diglycolamine, diethanolamine or the like, an alcohol such as ethanol, propylalcohol, ethylene glycol, pinacol or the like, an organic acid, an ether, a ketone, an amino acid, an ester, a thioalcohol and a thioether. A compound that may produce the above-described organic additive under the hydrothermal synthesis conditions may also be employed.

As a source of an alkali metal or an alkaline earth metal, there may be used a hydroxide, a halide, a sulfate, a nitrate, a carbonate or the like of an alkali metal such as sodium, potassium or the like or an alkaline earth metal such as magnesium, calcium or the like. Raw materials may contain a mineral acid such as sulfuric acid, nitric acid or the like as a pH adjusting agent in addition to the above-described compounds. An aqueous mixture containing one or more of the above-described compounds to be used as a raw material may be subjected to crystallization at temperatures of from 50° C. to 300° C., preferably from 100° C. to 250° C. under autogenous pressures for a retention period of from about 1 hour to 7 days, preferably from 1 to 5 days. The product obtained by the above-mentioned process may be subjected further to the modification treatment as needed. Accordingly, the crystalline aluminogallosilicate referred to herein may also include a variety of modified products obtainable by the modification treatment in addition to those producible by the hydrothermal synthesis.

The MASNMR (Magic Angle Spinning Nuclear Magnetic Resonance) analysis may give useful information on the elements present in the crystal structure of the crystalline aluminogallosilicate and on the composition thereof. For example, the $^{27}$Al-NMR analysis of an aluminosilicate gives information on the tetrahedral configuration in the anionic skeletal structure. The $^{29}$Si-NMR analysis gives information on the four tetrahedra (TO$_4$; T=Al, Si, Ga, etc.) adjacent to the (SiO$_4$) tetrahedron in the structure thereof. In the aluminogallosilicate described hereinabove, the $^{27}$Al-NMR and $^{71}$Ga-NMR analyses show that the Al and Ga elements of the tetrahedral configuration are present in the skeletal structure. From information provided by the $^{29}$Si-NMR analysis, the mole ratio of SiO$_2$ to (Al$_2$O$_3$+Ga$_2$O$_3$) in the crystal structure is computed.

One of the chemical characteristics of the crystalline aluminogallosilicate is its acid property. Generally, a degree of acidity may be determined by means of the temperature programmed desorption or the measurement for heat of adsorption using a basic substance such as ammonia, pyridine or the like. As the degrees of acidity balancing the aluminium and gallium used for synthesis are measured in the aluminogallosilicates, it is apparent that the aluminium and gallium are present in the anionic skeletal structure of the crystal structure and strong acid sites develop.

In a preferred aspect, the crystalline aluminogallosilicate according to the present invention is characterized in that aluminium is present in the amount ranging from 0.1% to 5.0% by weight and gallium in the amount ranging from 0.1% to 10.0% by weight in the skeletal structure, and the mole ratio of SiO$_2$ to (Al$_2$O$_3$+Ga$_2$O$_3$) is in the range from 15 to 300, the mole ratio of SiO$_2$ to Al$_2$O$_3$ being in the range from 16 to 870, more preferably from 16 to 400, and the mole ratio of SiO$_2$ to Ga$_2$O$_3$ being in the range from 18 to 2,000, more preferably from 18 to 500.

It is important that the aluminogallosilicate should have the composition represented in terms of molar ratios of oxides (calcined at 500° C. or higher) as follows:

$$aM_{2/n}O.bAl_2O_3.Ga_2O_3.cSiO_2.dH_2O$$

wherein M is a metal selected from an alkali metal, an alkaline earth metal and a mixture thereof, n is the valence of the metal M, a-d each represent a positive number of the following value:

a=(b+1)±3.0, preferably (b+1)±2.0;

b=1–6, preferably 2–4;

c=80–490;

d=1–200, preferably 1–50;

c/(b+1)=40–70, preferably 45–60; and c/b=46.7–140.

More specifically, in order to attain a high aromatics yield and a high activity retentivity as described hereinafter, the aluminogallosilicate must have the following molar ratios of oxides:

SiO$_2$/T$_2$O$_3$: 40–70
(T$_2$O$_3$=Al$_2$O$_3$+Ga$_2$O$_3$)
Al$_2$O$_3$/Ga$_2$O$_3$: 1–6
SiO$_2$/Ga$_2$O$_3$: 80–490
SiO$_2$/Al$_2$O$_3$: 46.7–140.

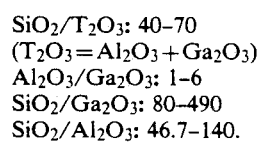

A SiO$_2$/T$_2$O$_3$ ratio of at least 40 is required in order that the aluminogallosilicate catalyst show a high retentivity in aromatics yield. The term "retentivity" or "activity retentivity" used herein is intended to refer to a percentage of the aromatics yield at 25 hours after the start of the olefin conversion based on the aromatics yield at 4 hours after the start of the olefin conversion. On the other hand, too high a SiO$_2$/T$_2$O$_3$ molar ratio in excess of 70 is undesirable because the aromatics yield at an initial stage of the reaction becomes low. A $SiO_2/T_2O_3$ of 45-60 gives especially good results and represents a preferred range.

An $Al_2O_3/Ga_2O_3$ of below 1 is disadvantageous because the activity rententivity becomes low. On the other hand, the $Al_2O_3/Ga_2O_3$ over 6 causes a reduction in initial aromatics yield. The $Al_2O_3/Ga_2O_3$ is preferably in ther range of 2-4. The aluminogallosilicate according to the present invention preferably has a surface area of at least 300 $m^2/g$.

Most preferable silicates are of the MFI type and/or of the MEL type. The MFI type and MEL type silicates belong to the structural type of the known zeolites of the kind published in "The Structure Commission of the International Zeolite Association" (*Atlas Of Zeolite Structure* Types; W. M. Meiyer and D. H. Olson (1978), Distributed by Polycrystal Book Service, Pittsburgh, Pa., U.S.A.).

The aluminogallosilicates obtainable by the hydrothermal synthesis as described above contain usually an alkali metal such as sodium, potassium or the like and/or an alkaline earth metal such as magnesium, calcium or the like, and they may be subjected to various conventional modification treatment as desired. For example, they may be converted to the ammonium form by the ion exchange in an aqueous solution containing an ammonium salt such as ammonium chloride, ammonium nitrate or the like and then subjected to ion exchange in an aqueous solution containing ions of a metal other than the alkali metal and the alkaline earth metal, thus introducing thereinto a desired metal other than the alkali metal and the alkaline earth metal. The aluminogallosilicate in the ammonium form may be converted to the hydrogen form by calcination at temperatures ranging from 350° C. to 650° C. Treatment of the aluminogallosilicate with hydrogen and/or steam is also effective in maintenance of the aromatization activity thereof. The modification treatment referred to herein may include a treatment that removes at least a portion of an alkali metal and/or an alkaline earth metal contained in the synthesized aluminogallosilicate, and such modification treatments are well known to the skilled in the art because they are conventional with respect to conventional crystalline zeolites.

The crystalline aluminogallosilicates according to the present invention may be utilized in various forms, and they may be formulated in the forms of powder and a molded product such as a granule, a sheet, a pellet or the like by means of the extrusion molding, spray drying, and tableting press molding after an addition of a binder such as alumina, silica or the like. The above-described modification treatments may also be applied to such molded products as well as to powdery products. Also a desired metal may be introduced into the molded products using the ion exchange method and the impregnation method. Metals capable of being introduced may include, for example, magnesium, calcium, strontium, barium, manganese, rhenium, iron, ruthenium, cobalt, rhodium, iridium, nickel, palladium, platinum, copper, silver, zinc, aluminium, indium, germanium, tin, lead, phosphorus, antimony, bismuth, selenium or the like.

The crystalline aluminogallosilicates according to the present invention exhibit extremely superior catalytic activities as catalysts for the preparation of high-octane gasoline using light hydrocarbons as raw materials, and their catalytic activities are higher than those of conventional aluminosilicates and gallosilicates.

In order to produce the high-octane gasoline using aluminogallosilicates in accordance with the present invention, light hydrocarbons are catalyzed with the crystalline aluminogallosilicate according to the present invention at temperatures ranging from 350° C. to 650° C. under hydrogen partial pressures of 5 $kg/cm^2$ or lower. In this case, the use of the crystalline aluminogallosilicates in the hydrogen form is preferred, and the aluminogallosilicates in the hydrogen form may be preferably carried with a metal constituent as an accessory constituent. Such a carrier metal as being capable of improving the catalytic activities may include, for example, magnesium, calcium, strontium, barium, lanthanum, cerium, titanium, vanadium, chromium, molybdenum, tungsten, manganese, rhenium, iron, ruthenium, cobalt, rhodium, iridium, nickel, palladium, platinum, copper, silver, zinc, aluminium, indium, germanium, tin, lead, phosphorus, antimony, bismuth, selenium or the like. These metals may be used singly or in combination with two or more, and the carrier quantity may be in the range from 0.1 to 10% by weight when reduced to a metal basis. As a method of causing a metal to be carried may be used conventional techniques such as the ion exchange method, impregnation method and so on. The aluminogallosilicates to be used as catalysts in accordance with the present invention may also be carried with one or more metals selected from magnesium, calcium, lanthanum, cerium, ruthenium and iridium in order to prevent coke from being accumulated. In this case, the carrier amount may be in the range from 0.01% to 5% by weight when reduced on a metal basis.

Reaction temperatures to be applied to the conversion reaction of the light hydrocarbons according to the present invention may be determined depending upon the compositions of the light hydrocarbons serving as a reactant, yields of the high-octane gasoline and so on, and they may range preferably from 350° C. to 650° C. If the reaction temperatures become lower, the production of byproducts such as light gases, e.g., methane, ethane or the like, can be prevented, but the yields of the high-octane gasoline are decreased. If the reaction temperatures become higher, the yields of the high-octane gasoline can be increased while the catalytic deactivation may be accelerated by means of coke or the like, thereby reducing the life of the catalyst. The reaction temperatures may range more preferably from 450° C. to 650° C. for the light hydrocarbons containing a n-paraffin as a major constituent, from 400° C. to 600° C. for the light hydrocarbons containing an isoparaffin as a major constituent, and from 350° C. to 550° C. for the light hydrocarbons containing an olefin as a major constituent.

In the conversion processes described above, no high pressures are particularly required because a sufficient yield of the high-octane gasoline can be attained under ambient pressures. However, if the reactants contain a large quantity of light gases such as ethane, propane or the like or in instances where a byproduct, hydrogen, or propane or butane is used as an LPG, it is economically advantageous to use elevated pressures as high as about 20 $kg/cm^2$. As reactions including the dehydrogenation proceed in the conversion of the light hydrocarbons to the high-octane gasoline, the hydrogen partial pressures balancing the reaction can be attained under reaction conditions without an addition of hydrogen. An intentional addition of hydrogen may have the advantages that the coke accumulation can be prevented and the catalyst life can be prolonged, but it is not necessarily advantageous because an increase of the hydrogen partial pressure may radically decrease the yields of the high-octane gasoline. It is accordingly preferred to restrict the hydrogen partial pressures to 5 kg/cm² or lower.

The modes of the reactions to be carried out for the conversion processes of the light hydrocarbons may be any mode of the fixed bed, moving bed and fluidized bed. The quantity of the reactants to be used for the fixed bed may range from 100 to 10,000 hr$^{-1}$, preferably from 100 to 2,000 hr$^{-1}$ as a gas space velocity. If the reaction mode other than the fixed bed is used, the catalytic period may be determined so as to become virtually the same as with the fixed bed.

The crystalline aluminogallosilicates according to the present invention are superior in catalytic activities with respect to the conversion reaction of the light hydrocarbons to the high-octane gasoline to conventional aluminosilicates and gallosilicates. Furthermore, the crystalline aluminogallosilicates according to the present invention are advantageous in terms of manufacturing costs because of a low content of gallia as compared to conventional gallosilicates. Moreover, they have properties as a solid acid superior to aluminosilicates and gallosilicates.

The crystalline aluminogallosilicates according to the present invention can be utilized as catalysts for the conversion reaction for the above-described light hydrocarbons. As a result of review on the passages of the conversion reaction of the light paraffinic hydrocarbons to aromatic hydrocarbons, it came to ensure that the efficient conversion of propane, contained in the raw material or produced in situ as a byproduct, to olefins leads eventually to a high yield of the aromatic hydrocarbons from the raw materials.

Upon investigation on the initial step of the reaction of propane, it was found that the dehydrogenation reaction and the cracking reaction occur competitively as illustrated below:

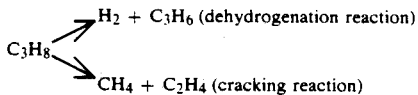

The cracking reaction forms methane, and a higher rate of the cracking reaction does not lead to an efficient utilization of carbon to aromatic compounds.

The catalytic cracking proceeds on the Bronsted acid sites, and the Bronsted acid sites in turn are activation sites necessary for the consecutive reactions, such as oligomerization, of olefins in the aromatization step of the olefins.

An extensive study on the preparation of catalysts effective for the aromatization reaction of the light hydrocarbons was made on the basis of the catalyst design that the catalyst should have a binary function in combination of dehydrogenation and acidity and that a selectivity of the dehydrogenation reaction is higher than that of the cracking reaction. As a result, the present invention was completed on the basis of the finding of the crystalline aluminogallosilicates as catalysts, the skeletal structure of which are constituted by the $SiO_2$, $AlO_4$ and $GaO_4$ tetrahedra.

On the model of the conversion reaction of propane and propylene, the crystalline aluminogallosilicate (Catalyst No. 1 in Table 1) according to the present invention is compared in catalytic properties to other catalysts (Catalysts Nos. 2–6 in Table 1). The results are shown in Table 2 below.

TABLE 1

| Catalyst Nos. | Compositions (% by weight) | |
|---|---|---|
| 1 | H-Aluminogallosilicate | |
| | Si/(Al + Ga) | 25.5 |
| | Si/Al | 37.1 |
| | Si/Ga | 81.5 |
| | Ga | 1.3 |
| 2 | H-Gallosilicate | |
| | Si/Ga | 40.2 |
| | Ga | 2.7 |
| 3 | 2.3% Ga/H-ZSM-5 | |
| | Si/Al | 31.6 |
| 4 | 0.4% Ga/H-ZSM-5 | |
| | Si/Al | 31.6 |
| 5 | H-ZSM-5 | |
| | Si/Al | 14.5 |
| 6 | H-ZSM-5 | |
| | Si/Al | 31.6 |

TABLE 2

| Catalyst Nos. | 1 | 2 | 3 | 4 | 5 | 6 |
|---|---|---|---|---|---|---|
| Reaction of Propane[1] Relative Conversion[2] | 8.4 | 1.8 | 4.5 | 3.5 | 5.6 | 1.0 |
| Selectivity (%)[3] | | | | | | |
| $C_3H_8 \to H_2 + C_3H_6$ | 80 | 85 | 80 | 75 | 25 | 20 |
| $C_3H_8 \to CH_4 + C_2H_4$ | 20 | 15 | 20 | 25 | 75 | 80 |
| Reaction of Propylene[4] | 22.6 | 5.4 | | 2.0 | 7.6 | 1.7 |
| Aromatics Yield (Cwt %) | 2.7 | 0.5 | | 0.6 | 5.4 | 1.4 |
| $C_1$–$C_4$ Yield (Cwt %) | | | | | | |

Notes:
[1]Temperature, 538° C.; Pressure, 1 atm.
[2]Calculated from data at GHSV = 34,200/h
[3]Extrapolated to conversion ~0
[4]Temperature, 500° C.; Pressure, 1 atm.; GHSV, 10⁶ h$^{-1}$; C₃'/Ar, 10/90 (mol/mol)

As apparent from the tables above, the crystalline aluminogallosilicates according to the present invention can be said to be highly superior in terms of the dehydrogenation function of paraffins and the cyclization and dehydrogenation functions of the olefins as the catalyst design has intended to perform the functions. In addition, the crystalline aluminogallosilicates according to the present invention can be employed as catalysts for isomerization, alkylation and disproportionation of hydrocarbons, the aromatization of methanol and so on by utilizing their properties as solid acids. They also may be used as adsorbents, like conventional aluminosilicates, by utilizing their physical adsorptive characteristics.

The present invention will be described more in detail by way of working examples.

EXAMPLE 1

Preparation of Aluminogallosilicates

A total number of 17 crystalline aluminogallosilicates were prepared in accordance with the following procedures.

A solution (I) was prepared from sodium silicate (J Sodium silicate #3: 28–30% by weight of $SiO_2$; 9–10% by weight of $Na_2O$; balance, water; Product of Nippon Kagaku Kogyo K. K.) in the amount shown under the column q-1 in Table 3 below and water in the amount shown under the column q-2 therein. Another solution (II) was prepared from $Al_2(SO_4)_3.14\sim18H_2O$ in the amount shown under the column q-3 in Table 3 below, Ga(NO₃)₃.9H₂O in the amount shown under the column q-4 therein, tetrapropylammonium bromide in the amount shown under the column q-5 therein, H₂SO₄ (97% by weight) in the amount shown under the column q-6 therein, NaCl in the amount shown under the column q-7 therein and water in the amount shown under the column q-8 therein.

The solution (II) was gradually poured into the solution (I) with stirring at room temperature, and the mixture was stirred with a mixer for 5 minutes. After the stirring, the mixture was placed in a stainless steel autoclave and subjected to crystallization at 180° C. under autogenous pressure.

The resultant gel was then charged to the autoclave that in turn was sealed and heated to 180° C. The gel was held for 5 days therein, and the crystalline product was separated from its mother liquor by filtration, washed five times with a 1-liter portion of water and then dried at 120° C. for 3 hours. The dried product was then calcined at 550° C. for 3 hours in air. After the calcined product was taken, it was filtered by suction and then washed five times with a 1-liter portion of water. The filtered solid material was dried at 120° C. for 3 hours and then calcined at 55° C. for 3 hours under air streams to produce each of the 17 aluminogallosilicates. The products were determined to be of the MFI structure type by X-ray diffraction. Table 3 below indicates the components of aqueous mixtures that are raw materials for aluminogallosilicates Al/Ga-1 to Al/Ga-17, respectively.

The mole ratios of the aluminogallosilicate may be represented by the following formula:

$$vSiO_2 \cdot wAl_2O_3 \cdot xGa_2O_3 \cdot yH_2O \cdot zH_2O$$

The compositions of the aluminogallosilicate are shown in Table 4 below.

TABLE 3

| Sample Nos. | Components of Aqueous Mixtures (grams) | | | | | | | | Time[1] (hrs) |
|---|---|---|---|---|---|---|---|---|---|
| | q-1 | q-2 | q-3 | q-4 | q-5 | q-6 | q-7 | q-8 | |
| Al/Ga-1 | 426.5 | 556.9 | 32.1 | 38.9* | 259.0 | 18.2 | 81.6 | 743.9 | 139 |
| Al/Ga-2 | 426.5 | 556.9 | 32.1 | 16.4* | 184.0 | 27.1 | 81.6 | 743.9 | 139 |
| Al/Ga-3 | 426.5 | 556.9 | 32.1 | 8.2* | 156.8 | 30.4 | 81.6 | 743.9 | 139 |
| Al/Ga-4 | 426.5 | 556.9 | 32.1 | 9.1 | 156.8 | 30.4 | 163.3 | 743.9 | 120 |
| Al/Ga-5 | 426.5 | 556.9 | 16.0 | 38.9* | 194.3 | 25.9 | 163.3 | 743.9 | 72 |
| Al/Ga-6 | 426.5 | 556.9 | 16.0 | 25.9* | 151.1 | 31.1 | 163.3 | 743.9 | 72 |
| Al/Ga-7 | 426.5 | 556.9 | 16.0 | 16.4* | 119.3 | 34.9 | 163.3 | 743.9 | 72 |
| Al/Ga-8 | 426.5 | 556.9 | 16.0 | 18.2 | 119.3 | 34.9 | 163.3 | 743.9 | 120 |
| Al/Ga-9 | 1706.1 | 2227.5 | 64.2 | 36.4 | 368.0 | 152.6 | 653.1 | 2975.7 | 72 |
| Al/Ga-10 | 426.5 | 556.9 | 16.0 | 9.1 | 92.3 | 42.0 | 163.3 | 743.9 | 120 |
| Al/Ga-11 | 426.5 | 556.9 | 16.0 | 3.0 | 73.8 | 40.3 | 163.3 | 743.9 | 120 |
| Al/Ga-12 | 106.6 | 139.2 | 2.0 | 0.8 | 13.5 | 11.1 | 40.8 | 186.0 | 120 |
| Al/Ga-13 | 213.3 | 278.4 | 3.4 | 4.6 | 27.3 | 21.3 | 81.6 | 372.0 | 72 |
| Al/Ga-14 | 213.3 | 278.4 | 32.1 | 1.5 | 134.1 | 8.5 | 40.8 | 372.0 | 139 |
| Al/Ga-15 | 213.3 | 278.4 | 8.0 | 36.0 | 140.3 | 7.8 | 40.8 | 372.0 | 139 |
| Al/Ga-16 | 213.3 | 278.4 | 8.0 | 0.3 | 33.2 | 20.6 | 81.6 | 372.0 | 24 |
| Al/Ga-17 | 213.3 | 278.4 | 0.6 | 1.5 | 7.1 | 23.7 | 81.6 | 372.0 | 72 |

Notes:
*Ga(NO₃)₃.nH$_{n/2}$O (18.51% as Ga);
[1]Time for crystallization

TABLE 4

| Sample Nos. | Mole Ratios Of Aluminogallosilicates | | | | | | | | |
|---|---|---|---|---|---|---|---|---|---|
| | v | w | x | y | z | SiO₂/ Al₂O₃ | SiO₂/ Ga₂O₃ | SiO₂/Al₂O₃ + Ga₂O₃ | Catl. Nos.* |
| Al/Ga-1 | 41.0 | 1.08 | 1.00 | 1.57 | 7.39 | 38.0 | 41.0 | 19.8 | I |
| Al/Ga-2 | 94.6 | 2.52 | 1.00 | 2.32 | 13.40 | 37.5 | 94.6 | 26.8 | II |
| Al/Ga-3 | 174.3 | 4.59 | 1.00 | 3.63 | 31.16 | 38.0 | 174.3 | 31.2 | III |
| Al/Ga-4 | 172.0 | 4.56 | 1.00 | 5.53 | 15.86 | 37.7 | 172.0 | 31.0 | IV |
| Al/Ga-5 | 40.6 | 0.47 | 1.00 | 0.98 | 9.24 | 86.4 | 40.6 | 27.6 | V |
| Al/Ga-6 | 54.8 | 0.72 | 1.00 | 1.27 | 9.91 | 76.1 | 54.8 | 31.8 | VI |
| Al/Ga-7 | 83.1 | 1.17 | 1.00 | 1.64 | 13.21 | 71.0 | 83.1 | 38.4 | VII |
| Al/Ga-8 | 74.8 | 1.09 | 1.00 | 1.73 | 6.39 | 68.6 | 74.8 | 35.8 | VIII |
| Al/Ga-9 | 157.3 | 2.26 | 1.00 | 2.31 | 17.37 | 69.6 | 157.3 | 48.4 | IX |
| Al/Ga-10 | 162.9 | 2.20 | 1.00 | 2.62 | 34.04 | 74.0 | 162.9 | 50.9 | X |
| Al/Ga-11 | 437.5 | 6.09 | 1.00 | 5.64 | 23.62 | 71.8 | 437.5 | 61.6 | XI |
| Al/Ga-12 | 445.5 | 3.11 | 1.00 | 6.49 | 42.75 | 143.2 | 445.5 | 108.4 | XII |
| Al/Ga-13 | 144.5 | 0.85 | 1.00 | 1.74 | 19.66 | 170.0 | 144.5 | 78.0 | XIII |
| Al/Ga-14 | 403.1 | 25.12 | 1.00 | 17.68 | 54.00 | 16.0 | 403.1 | 15.4 | XIV |
| Al/Ga-15 | 24.3 | 0.36 | 1.00 | 1.47 | 6.48 | 67.5 | 24.3 | 17.9 | XV |
| Al/Ga-16 | 1984.3 | 28.16 | 1.00 | 25.35 | 157.61 | 70.5 | 1984.3 | 68.1 | XVI |
| Al/Ga-17 | 446.5 | 0.52 | 1.00 | 6.12 | 23.73 | 858.7 | 446.5 | 293.8 | XVII |

Notes:
*Catalyst Numbers of Aluminogallosilicates in the H-form according to the present invention

EXAMPLE 2

Preparation of Catalysts

Each of the aluminogallosilicates Al/Ga-1 to Al/Ga-17 obtained in Example 1 was blended with alumina powder (Cataloid AP; Catalyst & Chemicals Ind. Co., Ltd.) and additional water. The mixture was blended in proportions to give about 73% aluminogallosilicate and about 27% Al₂O₄ in the final product. The blended mixture was then extruded through about 1/32" opening die plate. The extrudate was dried at 120° C. for 3 hours in air and then calcined at 550° C. or 3 hours under air streams.

After cooling, the extrudate was ion-exchanged four times at 100° C., each for two hours with a 2.2N ammonium nitrate aqueous solution at the rate of 5 ml per 100 grams of the calcined extrudate. The resultant NH$_4^+$-form extrudate was washed, dried at about 120° C. for 3 hours in air and then calcined at about 550° C. in air to give the H-form aluminogallosilicate catalyst No. I to XVII in the H-form as shown in Table 4 above.

For comparative purposes, using the seven crystalline aluminosilicates (Al-1 to Al-7) and the nine crystalline gallosilicates (Ga-1 to Ga-9), each having the mole ratios indicated in Table 5 below, the H-form aluminosilicates (H-[Al-1] to H-[Al-7]) and the H-form gallosilicates (H-[Ga-1] to H-[Ga-9]) were prepared in substantially the same manner as above. These aluminosilicates and gallosilicates were identified to be of the MFI structure type by X-ray diffraction analysis.

Figure 1:
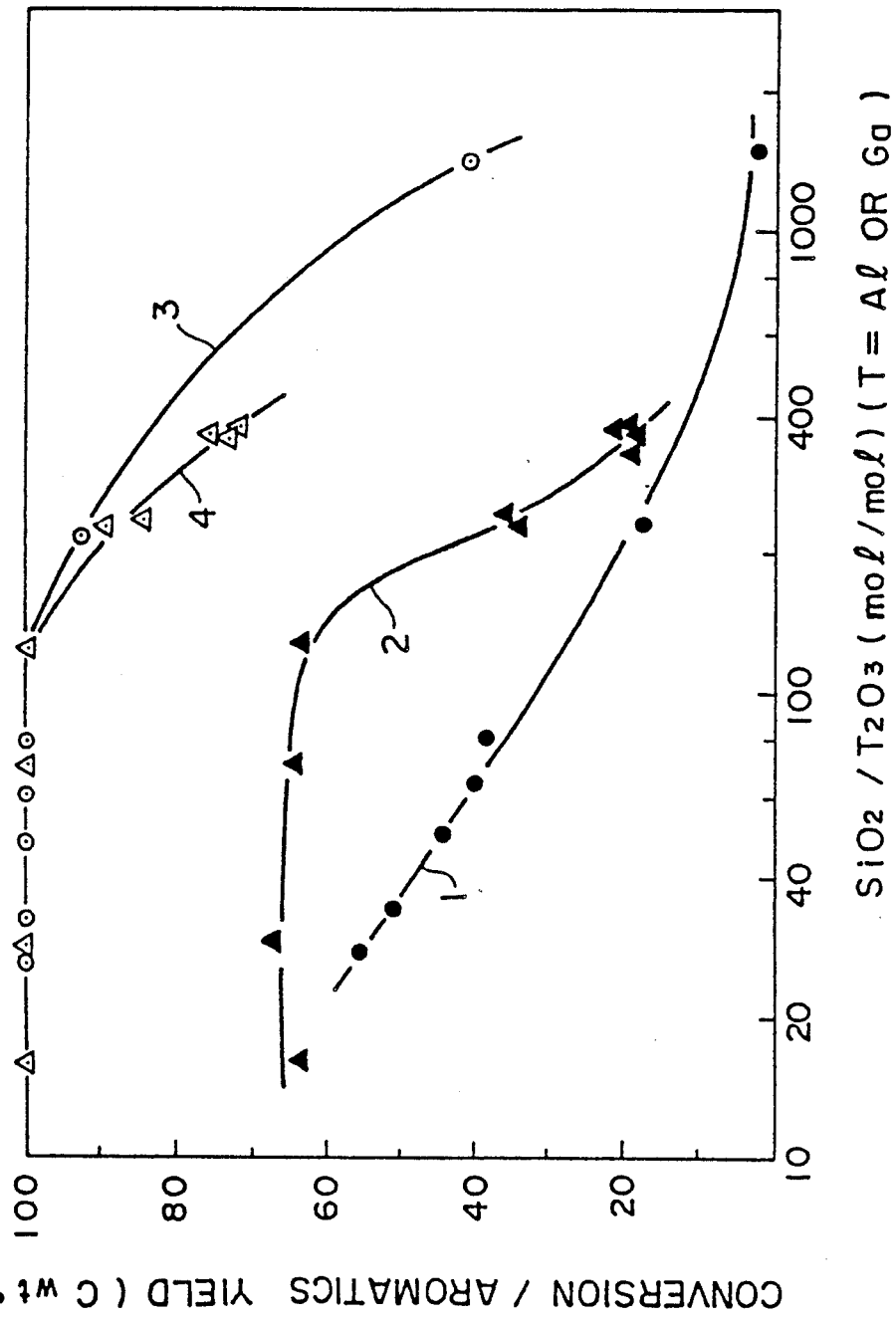

FIG. 1 shows the reaction data of Comparative Examples 1 to 16 in Table 8 below.

In the drawing, the curved lines 1 and 2 indicate aromatics yields of the aluminosilicates and the gallosilicates on the C-standard basis, respectively. It is to be noted from the data that the gallosilicates are high in the aromatics yield than the aluminosilicates.

Figure 2:
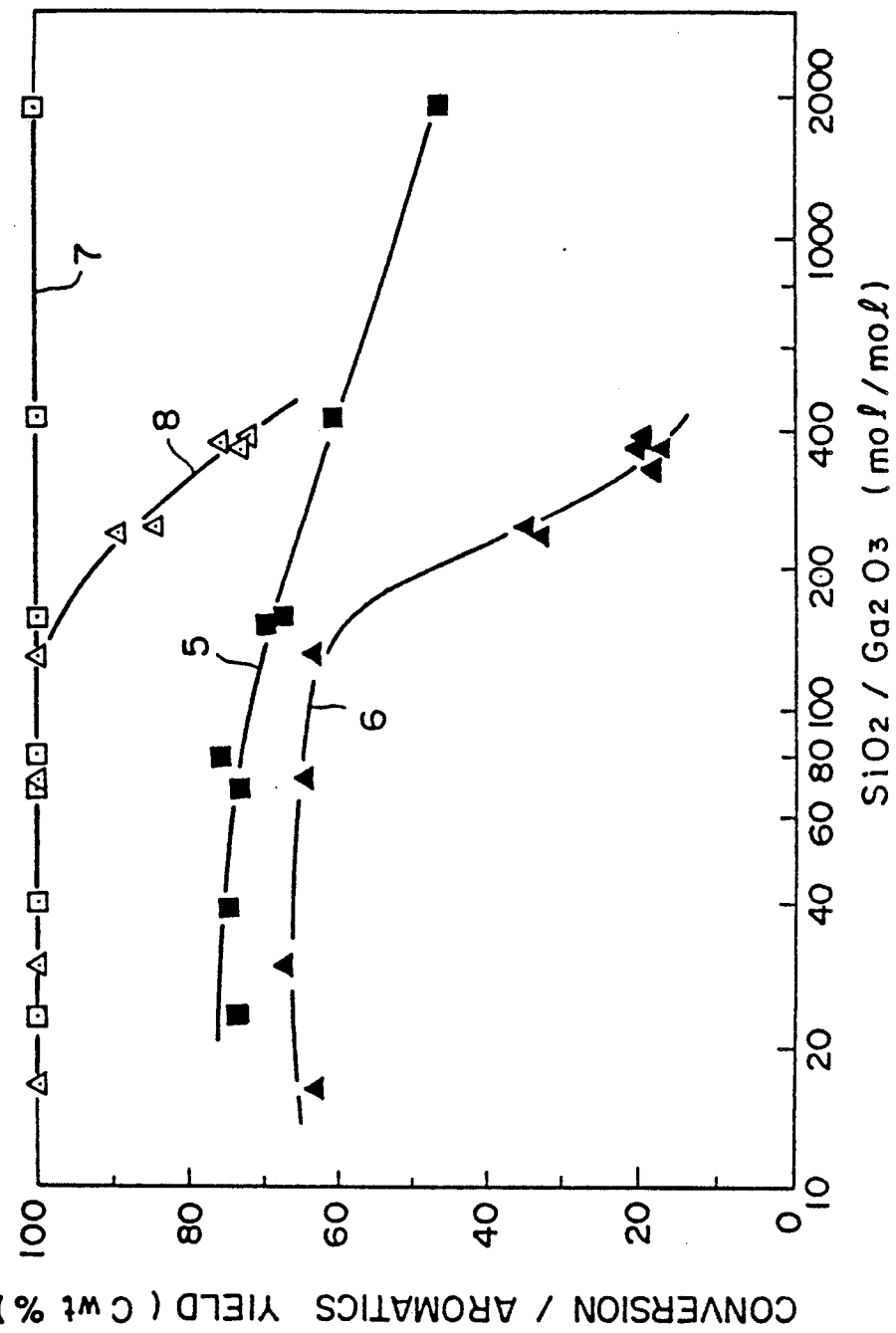
FIG. 2 is a graph showing the relationships of $SiO_2/Ga_2O_3$ vs. conversion and aromatics yield of the aluminogallosilicate of the present invention and the comparing gallosilicate.

FIG. 2 show the aromatics yields and the conversion for the aluminogallosilicates according to the present invention (curved lines 5 and 7, respectively) and those for the gallosilicates (curved lines 6 and 8, respectively) for comparative purposes. This figure demonstrates that the aluminogallosilicates are remarkably superior catalysts.

Figure 3:
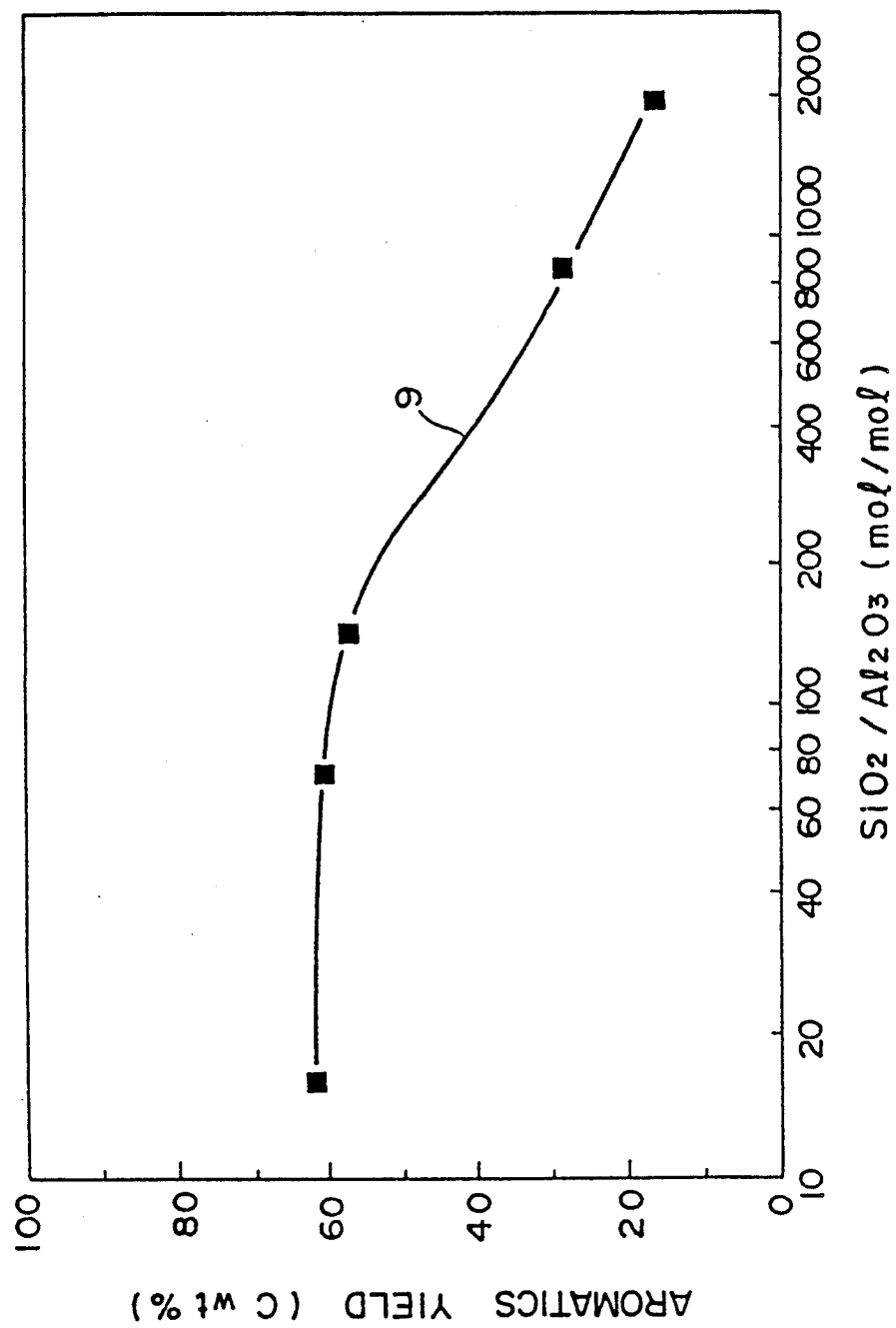
FIG. 3 is a graph showing the relationship of $SiO_2/Al_2O_3$ vs. aromatics yield of the comparing aluminosilicate.

FIG. 3 demonstrates a variation in aromatics yields vs. $SiO_2/Al_2O_3$ for the aluminogallosilicate catalyst containing in its skeleton gallium in the amount virtu-

TABLE 5

| Sample Nos. | SiO$_2$ | Al$_2$O$_3$ | Ga$_2$O$_3$ | Na$_2$O | H$_2$O | SiO$_2$/Al$_2$O$_3$ | SiO$_2$/Ga$_2$O$_3$ | Catlyst Nos. |
|---|---|---|---|---|---|---|---|---|
| Al-1 | 29.1 | 1.00 | — | 0.57 | 3.89 | 29.1 | — | H-[Al-1] |
| Al-2 | 35.1 | 1.00 | — | 1.02 | 2.86 | 35.1 | — | H-[Al-2] |
| Al-3 | 51.2 | 1.00 | — | 0.91 | 5.27 | 51.2 | — | H-[Al-3] |
| Al-4 | 66.2 | 1.00 | — | 0.93 | 12.12 | 66.2 | — | H-[Al-4] |
| Al-5 | 81.5 | 1.00 | — | 1.00 | 7.26 | 81.5 | — | H-[Al-5] |
| Al-6 | 232.2 | 1.00 | — | 0.25 | 29.10 | 232.2 | — | H-[Al-6] |
| Al-7 | 1491.0 | 1.00 | — | 16.39 | 132.06 | 1491.0 | — | H-[Al-7] |
| Ga-1 | 18.0 | 0.01* | 1.00 | 1.09 | 3.72 | 1800 | 18.0 | H-[Ga-1] |
| Ga-2 | 29.9 | 0.01* | 1.00 | 0.58 | 3.54 | 2990 | 29.9 | H-[Ga-2] |
| Ga-3 | 80.4 | 0.05* | 1.00 | 0.89 | 9.02 | 1608 | 80.4 | H-[Ga-3] |
| Ga-4 | 135.7 | 0.06* | 1.00 | 1.92 | 16.52 | 2262 | 135.7 | H-[Ga-4] |
| Ga-5 | 255.5 | 0.12* | 1.00 | 3.41 | 14.35 | 2129 | 255.5 | H-[Ga-5] |
| Ga-6 | 247.5 | 0.13* | 1.00 | 3.37 | 11.39 | 1904 | 247.5 | H-[Ga-6] |
| Ga-7 | 398.6 | 0.21* | 1.00 | 5.68 | 20.76 | 1898 | 398.6 | H-[Ga-7] |
| Ga-8 | 378.4 | 0.18* | 1.00 | 5.39 | 19.25 | 2102 | 378.4 | H-[Ga-8] |
| Ga-9 | 352.9 | 0.17* | 1.00 | 4.89 | 42.75 | 2076 | 352.9 | H-[Ga-9] |
| (Al-1) + (Ga-3) 158.5 | 2.72 | 1.00 | 2.42 | 18.87 | 58.3 | 158.5 | | H-([Al-1] + [Ga-3]) |

EXAMPLES 3 TO 19 AND COMPARATIVE EXAMPLES 1 TO 18

Conversion of n-Hexane

Using the H-form aluminogallosilicate catalysts Nos. I to XVII, the conversion reaction of n-hexane was conducted using a flow reactor under the following reaction conditions: temperature, 538° C.; pressure, 1 atm.; hydrogen partial pressure, 0.5 kg/cm$^2$ or lower; LHSV, 2 hr$^{-1}$; catalyst amount, 3 ml (sieved to pass 16 to 24 mil); reaction time, 1 hour.

The resultant products were analyzed by a gas chromatograph connected to the reactor.

For comparative purposes, the above procedures were followed with the exception that the H-form aluminosilicates Nos. H-[Al-1] to H-[Al-7] and the H-form gallosilicate Nos. H-[Ga-1] to H-[Ga-9] indicated in Table 5 above were used as catalysts.

Furthermore, an equimolar mixture of the aluminosilicate H-[Al-1] with the gallosilicate H-[Ga-3] was treated in virtually the same manner as in Example 2 to give the H-form aluminosilicate/gallosilicate H-([Al-1]+[Ga-3]). The above test was conducted using this as a catalyst.

Tables 7 and 9 show compiled reaction data with respect to the aluminogallosilicates. Tables 8 and 9 show compiled reaction data with respect to the aluminosilicates and the gallosilicates used for comparative purposes.

ally equivalent to the H-form gallosilicate catalyst H-[Ga-7] used for comparative purposes.

From data from the catalysts obtained in Example 12 and Comparative Example 17, it is indicated that the aluminogallosilicate according to the present invention is different from a physical mixture of the aluminosilicate with the gallosilicate.

EXAMPLE 10

Using the H-form aluminogallosilicate No. X prepared in Example 2, as shown in Table 4, the reaction was carried out using light naphtha having the composition as shown in Table 6 below, under the reaction conditions: temperature, 538° C.; pressure, 3 kg/cm$^2$G; hydrogen partial pressure, 1 kg/cm$^2$ or lower; LHSV, 1 hr$^{-1}$; gas present, N$_2$ (flow rate: 10N liter/hour); catalyst amount, 20 cc.

TABLE 6

| Components | % (by weight) |
|---|---|
| n-butane | 8.0 |
| cyclopentane | 2.0 |
| isopentane | 17.0 |
| n-pentane | 25.0 |
| benzene | 4.0 |
| methylcyclopentane | 1.0 |
| cyclohexane | 1.0 |
| 2,3-dimethylbutane | 2.0 |
| 2-methylpentane | 12.5 |
| 3-methylpentane | 7.5 |
| n-hexane | 17.0 |

TABLE 6-continued

| Components | % (by weight) |
|---|---|
| others | 3.0 |

$C_3'$: propylene
$C_4$: butane
$C_4'$: butene
$\geq C_5$: hydrocarbons with carbon atoms of 5 or more

TABLE 7

| Items | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|
| Catalyst Nos. | I | II | III | IV | V | VI | VII | VIII | IX |
| Conversion (%) | 100 | 100 | 100 | 100 | 100 | 100 | 100 | 100 | 100 |
| Aromatics Yield (C wt %) | 74.4 | 70.4 | 70.1 | 71.4 | 75.0 | 68.3 | 75.9 | 73.4 | 70.5 |

| Items | Ex. 12 | Ex. 13 | Ex. 14 | Ex. 15 | Ex. 16 | Ex. 17 | Ex. 18 | Ex. 19 |
|---|---|---|---|---|---|---|---|---|
| Catalyst Nos. | X | XI | XII | XIII | XIV | XV | XVI | XVII |
| Conversion (%) | 100 | 100 | 100 | 100 | 100 | 100 | 100 | 86 |
| Aromatics Yield (C wt %) | 67.2 | 60.6 | 57.5 | 71.6 | 62.0 | 74.0 | 46.3 | 28.5 |

TABLE 8

| Items | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex.9 |
|---|---|---|---|---|---|---|---|---|---|
| Catalyst No. | H-[Al-1] | H-[Al-2] | H-[Al-3] | H-[Al-4] | H-[Al-5] | H-[Al-6] | H-[Al-7] | H-[Ga-1] | H-[GA-2] |
| Conversion (%) | 100 | 100 | 100 | 100 | 100 | 92.7 | 40.5 | 100 | 100 |
| Aromatics Yield (C wt %) | 55.3 | 50.9 | 44.4 | 40.1 | 38.2 | 17.1 | 2.4 | 63.8 | 67.7 |

| Items | Comp. Ex. 10 | Comp. Ex. 11 | Comp. Ex. 12 | Comp. Ex. 13 | Comp. Ex. 14 | Comp. Ex. 15 | Comp. Ex. 16 | Comparative Example 17 | |
|---|---|---|---|---|---|---|---|---|---|
| Catalyst No. | H-[Ga-3] | H-[Ga-4] | H-[Ga-5] | H-[Ga-6] | H-[Ga-7] | H-[Ga-8] | H-[Ga-9] | H-([Al-1] + [Ga-3]) | |
| Conversion (%) | 100 | 99.8 | 84.2 | 89.1 | 71.6 | 72.8 | 75.8 | 100 | |
| Aromatics Yield (C wt %) | 64.2 | 63.6 | 32.8 | 34.7 | 16.7 | 17.0 | 19.7 | 57.5 | |

TABLE 9

| Item | Ex. 6 | Ex. 10 | Ex. 12 | Ex. 20 | Comp. Ex. 1 | Comp. Ex. 10 | Comp. Ex. 17 |
|---|---|---|---|---|---|---|---|
| Catalyst Nos. | IV | VIII | X | X | H-[Al-1] | H-[Ga-3] | H-([Al-1] – [Ga-3]) |
| Conversion (%) | 100 | 100 | 100 | — | 100 | 100 | 100 |
| Aromatics Yield (C wt %) | 71.4 | 73.4 | 67.2 | — | 55.3 | 64.2 | 57.5 |
| Yields (% by weight) | | | | | | | |
| Hydrogen | 3.22 | 3.03 | 2.96 | 3.11 | 1.65 | 3.17 | 2.12 |
| Hydrocarbons | | | | | | | |
| $C_1$ | 13.10 | 9.32 | 9.21 | 8.78 | 15.31 | 6.24 | 11.12 |
| $C_2$ | 8.37 | 6.12 | 7.91 | 9.96 | 13.67 | 6.80 | 12.01 |
| $C_2'$ | 1.54 | 1.56 | 2.10 | 1.60 | 2.54 | 3.31 | 2.71 |
| $C_3$ | 6.78 | 10.18 | 13.55 | 17.90 | 14.33 | 15.13 | 16.85 |
| $C_3'$ | 0.72 | 0.95 | 1.26 | 0.40 | 1.08 | 2.37 | 1.35 |
| $C_4$ | 0.11 | 0.22 | 0.33 | 2.49 | 0.30 | 2.73 | 0.41 |
| $C_4'$ | 0.06 | 0.11 | 0.19 | 0.45 | 0.22 | 0.58 | 0.23 |
| $\geq C_5$ | 66.05 | 68.47 | 62.41 | 55.35 | 50.94 | 59.56 | 53.06 |
| Benzene | 20.34 | 15.95 | 16.64 | 11.50 | | | |
| Toluene | 26.10 | 27.08 | 25.05 | 22.02 | | | |
| Xylene | 8.94 | 12.69 | 10.65 | 11.53 | | | |
| $C_9$ Arom. | 1.58 | 1.73 | 1.67 | 2.27 | | | |
| $C_{10}$ Arom. | 4.25 | 5.18 | 3.95 | 0.78 | | | |
| $C_{11}^+$ Arom. | 4.81 | 5.82 | 4.33 | 4.82 | | | |

Table 9 below shows compiled data of the reactions carried out above. The data for Example 20 were obtained in 19 hours after the start of the reaction. In the Table, references to hydrocarbons mean the following:
$C_1$: methane
$C_2$: ethane
$C_2'$: ethylene
$C_3$: propane

EXAMPLE 21

Comparison with Ga-on-Aluminosilicates

Using a $Ga(NO_3)_3$ aqueous solution, a catalyst for comparison was prepared by drying and calcinating as in Example 2 to carry a $NH_4$-form aluminosilicate, $NH_4$-[Al-4], with Ga.

The resulting catalyst was subjected to conversion of n-hexane as in Example 3. Table 10 below and FIG. 4 show the results.

TABLE 10

| Catalyst Nos. | H-[Al-4] | 0.3 wt % Ga[Al-4] | 2.3 wt % Ga[Al-4] | 2.7 wt % Ga[Al-4] | 8.2 wt % Ga[Al-4] |
| --- | --- | --- | --- | --- | --- |
| Convrsn (%) | 100 | 100 | 100 | 100 | 100 |
| Aromatics Yield (C wt %) | 40.1 | 56.2 | 59.1 | 57.3 | 65.9 |

Figure 4:
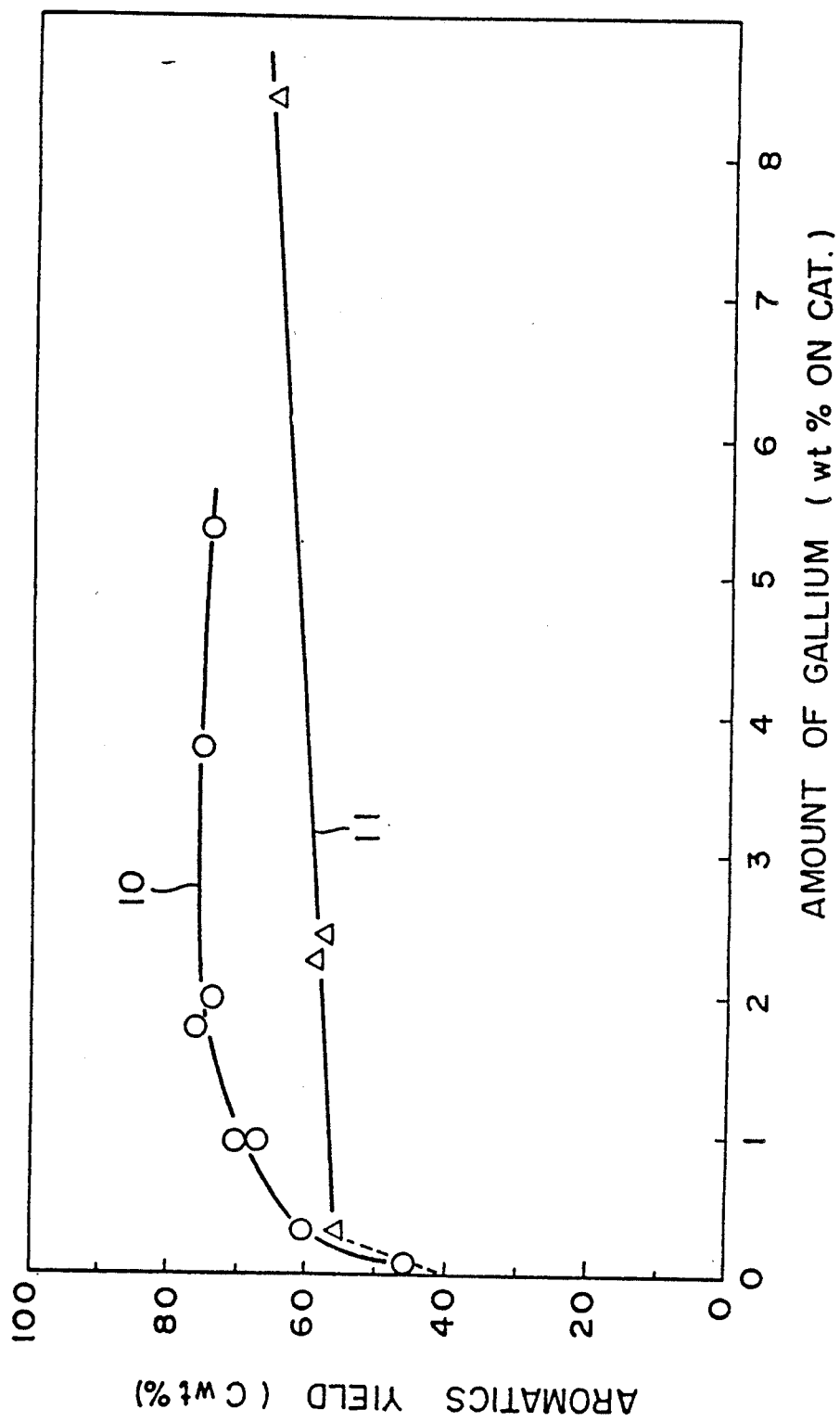
FIG. 4 is a graph showing the relationships of the gallium concentrations and aromatics yields of the H-form aluminogallosilicate according to the present invention with those of the comparing H-form aluminosilicate carried with gallium.

FIG. 4 shows the results of the conversion reaction obtained by the aluminogallosilicate catalyst (curved line 10) in comparison with those obtained by the aluminosilicate Al-4 (curved line 11) with the aluminium in the skeleton in the amount virtually equivalent to that of the latter. As apparent from FIG. 4, the aluminogallosilicate according to the present invention has a higher aromatization activity than the aluminosilicate carried with gallium.

It is also indicated in Tables 1 and 2 that the catalyst performance of the aluminogallosilicate is different from that of the Ga-on-aluminosilicate.

EXAMPLE 22

Preparation of Aluminogallosilicates of the MEL Structure Type and Their Catalysts A solution (I) was prepared from 464.5 g of sodium silicate (J Sodium silicate #3; SO$_2$: 28-30% by weight; Na$_2$O: 9-10% by weight; balance, water; Nippon Kagaku Kogyo K. K.) and 520 g of water. A solution (II) was prepared from 17.0 g of Al$_2$(SO$_4$)$_3$.14–18H$_2$O, 8.7 g of Ga(NO$_3$)$_3$.9H$_2$O, 143.4 g of tetrabutylammonium bromide, 43.3 g of H$_2$SO$_4$ (97% by weight) and 550 g of water.

The solution (II) was poured gradually into the solution (I) at room temperature, and the mixture was allowed to stand overnight in a sealed container and then stirred for 5 minutes with a mixer.

After stirring, the mixture was placed in a stainless steel autoclave and subjected to crystallization at 120° C. for 5 days and then at 180° C. for 1 day under autogenous pressure. The product was then filtered by suction, and it was washed with water and filtered. This procedure was repeated five times. The resultant solid substance was dried at 120° C. for 3 hours and then calcined at 550° C. for 3 hours under air streams to give an aluminogallosilicate.

The product was identified to be of the MEL structure type by X-ray diffraction. And the mole ratios of the aluminogallosilicate were as follows:

162.9SiO$_2$:2.58Al$_2$O$_3$:Ga$_2$O$_3$:3.03H$_2$O:16.2H$_2$O

Preparation of Catalysts

The resultant aluminogallosilicate was then blended with alumina powder (Cataloid AP: Catalyst & Chemicals Ind. Co., Ltd.) and additional water. The aluminogallosilicate and the Al$_2$O$_3$ were then blended in proportions to give ca. 73% aluminogallosilicate and ca. 27% Al$_2$O$_3$ in the final product.

The mixture was then extruded through an about 1/32" opening die plate. The extrudate was dried at about 120° C. for 3 hours in air and then calcined at about 550° C. for 3 hours in air. After cooling, the extrudate was subjected to ion exchange four times, each for 2 hours with 5 ml of a 2.2N ammonium nitrate solution at 100° C. per gram of the calcined extrudate. The resultant NH$_4$-form extrudate was then washed, dried at about 120° C. in air and again calcined at about 550° C. for 3 hours in air to give a H-form aluminogallosilicate.

EXAMPLE 23

Conversion of n-Hexane

Using the H-form aluminogallosilicate obtained in Example 22 as a catalyst, the conversion reaction of n-hexane was carried out in the same manner as in Example 3.

The reaction results were 100% for a conversion rate and 71.5 C % by weight for an aromatics yield.

EXAMPLE 24

The aluminogallosilicate Al/Ga-9 as shown in Table 4 was blended with silica sol (Cataloid SI-350: SiO$_2$, 30% by weight; Catalyst & Chemicals Ind. Co., Ltd.) and additional water. The aluminogallosilicate and the SiO$_2$ were blended in proportions to give ca. 73% aluminogallosilicate and ca. 27% SiO$_2$ in the final product.

The mixture was then dried and calcined as previously described. The calcined product was broken and sieved to pass 16 to 24 mesh.

The H-form aluminogallosilicate catalyst was prepared as described in Example 2.

Using the H-form aluminogallosilicate above as a catalyst, the conversion reaction was carried out in substantially the same manner as described in Example 3. The results were 100% for a conversion rate and 66.3 C % by weight.

EXAMPLE 25

Dependency on Reaction Temperatures

Figure 5:
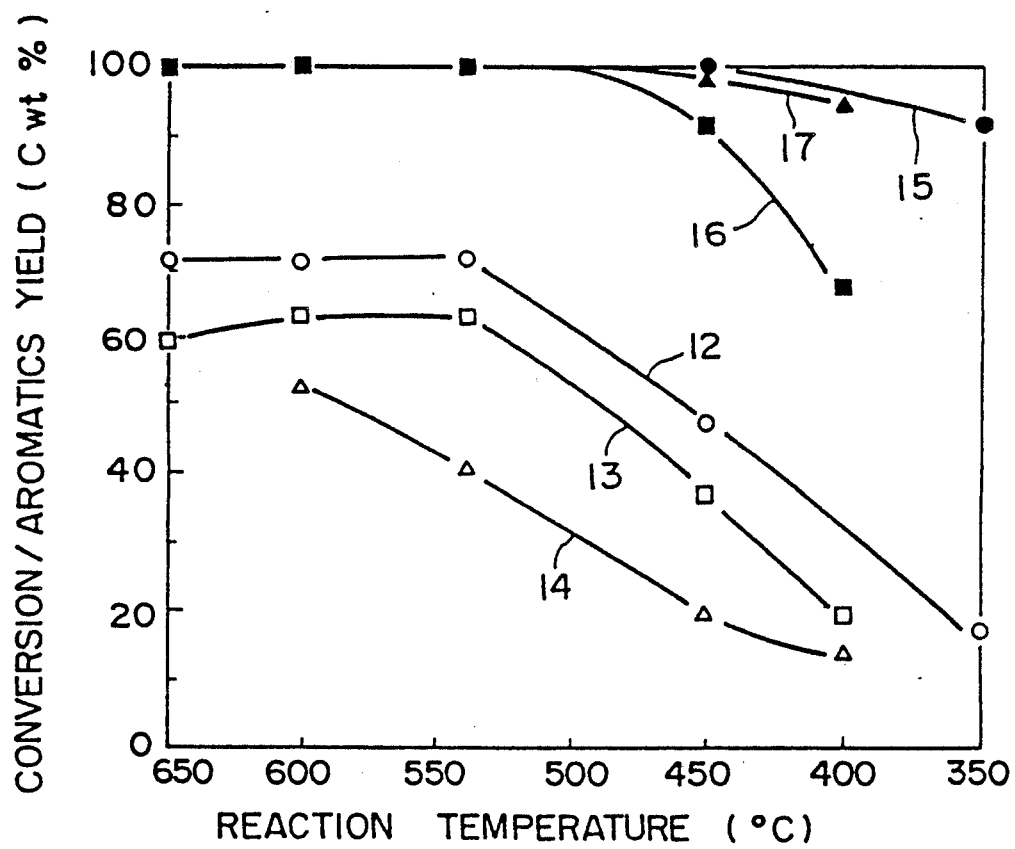
FIG. 5 is a graph showing the relationships of reaction temperatures vs. conversion and aromatics yields of the aluminogallosilicate according to the present invention and the comparing aluminosilicate and gallosilicate.

FIG. 5 shows the relationships of the aromatics yields (curved line 12) and the conversion rates of n-hexane (curved line 15) vs. reaction temperature for the aluminogallosilicate catalyst IX as shown in Table 4 with the aromatics yields (curved lines 13 and 14, respectively) and the conversion rates (curved lines 16 and 17, respectively) for the aluminosilicate catalyst H-[Al-4] as shown in Table 5 and the gallosilicate catalyst H-[Ga-3] as shown in Table 5.

Reaction conditions and procedures were the same as described in Example 3 except temperatures.

It was found that the aluminogallosilicate was higher in an aromatization activity than the gallosilicate that in turn was higher than the aluminosilicate in the whole temperature areas tested and consequently that the aluminogallosilicate catalyst according to the present invention was superior to the others.

EXAMPLE 26

Effects of H$_2$ Treatment

In order to confirm the effects of the pre-treatment with hydrogen on the conversion of n-hexane, the aluminogallosilicate was subjected to pre-treatment with hydrogen under conditions: temperature, 600° C.; pressure, 1 atm.; treatment time, 2 hours; and hydrogen flow rate, 100 cc/minute.

The conversion reaction of n-hexane was carried using the aluminogallosilicate IX as shown in Table 4 under the following conditions: temperature, 538° C.; pressure, 1 atm.; LHSV, 2 hr⁻¹; and reaction time, 25 hours.

Table 11 below and FIG. 6 indicate the reaction results.

TABLE 11

| | Treatment with H | | No H Treatment | |
|---|---|---|---|---|
| Times (hrs) | Convsn (%)[1] | Aromatics Yield (C wt %)[2] | Convsn (%)[3] | Aromatics Yield (C wt %)[4] |
| 1 | 100 | 66.5 | 100 | 67.6 |
| 4 | 100 | 65.2 | 100 | 67.3 |
| 7 | 100 | 64.2 | 100 | 65.8 |
| 10 | 100 | 62.9 | 100 | 63.8 |
| 13 | 100 | 62.1 | 100 | 62.2 |
| 16 | 100 | 61.0 | — | — |
| 19 | 100 | 59.7 | 99.9 | 60.9 |
| 22 | 100 | 58.7 | 99.9 | 55.3 |
| 25 | 100 | 57.7 | 99.9 | 51.6 |

Notes:
[1] curved line 19 in FIG. 6 curved line 18 in FIG. 6 curved line 21 in FIG. 6 curved line 20 in FIG. 6

As shown in FIG. 6, it was confirmed that the hydrogen treatment gave the effect on the maintenance of the aromatization activity for the aluminogallosilicate catalysts. The effect of the hydrogen treatment on the stability of the gallium and aluminium incorporated into the crystal skeleton will be indicated in Example 27.

EXAMPLE 27

Stability of Catalysts

In order to confirm the stability of the aluminium and the gallium in the crystal skeleton of the aluminogallosilicate, the test was conducted in comparison with an aluminosilicate carried with gallium under the reaction conditions as will be shown in Table 12 below.

TABLE 12

| Temperature | 570° C. |
|---|---|
| Pressure | 3 kg/cm²G |
| Gas used | Hydrogen |
| Flow rate | 100 Nl/hour |
| GHSV | ca. 33,000 hr⁻¹ |
| Flow time | 72 hours |
| Catalyst amount | 3 ml |

The experiment was carried out using a reactor filled with the catalyst. After the treatment under the above conditions, the specimens were subjected to X-ray fluorescence analysis to measure degrees of the desorption of the aluminium and gallium. Table 13 below shows the test. As will be shown in the table, it was confirmed that no desorption of the aluminium and gallium in the crystal skeleton of the aluminogallosilicate was recognized.

TABLE 13

| | Desorption Degree (%)* | | Elemental Analysis** |
|---|---|---|---|
| Catalyst | Ga | Al | of Fresh Catalyst (wt %) |
| X (shown in Table 4) | 0 | 0 | Skeletal Ga: 1.27 Skeletal Al: 1.08 |
| Ga-ZSM-5 | 12 | 0 | Carried-on Ga: 8.18 Skeletal Al: 1.24 |

Notes:
*calculated on the basis of the peak height of X-ray fluorescence analysis by using Si as a standard
**values obtained by the chemical analysis

EXAMPLE 28

Reaction/Regeneration Cycle Test

Tests for the regeneration of the catalyst were carried out by repeating the burning of coke on the aluminogallosilicate catalyst in dilute air after the reaction. The reaction and regeneration conditions are shown respectively in Tables 14 and 15.

FIG. 7 shows the compiled test results. It was found that the aromatization activity was maintained to virtually constant levels as the conversion rates were almost 100% as shown by the curved line 22, the aromatics yields were about 64 C % by weight as shown by the curved line 23, and the hydrogen yields were about 4.5% by weight as shown by the curved line 24.

TABLE 14

| Raw material | n-hexane |
|---|---|
| Reaction temp. | 538° C. |
| Reaction Ressure | 1 atm. |
| LHVS | 1.0 hr⁻¹ |
| Reaction time | 60 minutes |
| Catalyst used | X (as shown in Table 4) |

TABLE 15

| Reaction | 60 minutes; 538° C. |
|---|---|
| Lowering of temp. | 15 minutes; 450° C.; Ar 1,000 ml/minute |
| Elevation of temp. | 15 minutes; 450° C.; Ar/Air, 50/50 |
| Regeneration | 150 minutes; 538° C.; 42STP ml/minute |
| Replacement | 30 minutes; 538° C.; Ar 1000 ml/minute |

EXAMPLE 29

Conversion of Ethane, Propane and Butane

The conversion of ethane, propane and butane was carried out using the aluminogallosilicates IV, VIII and IX as shown in Table 4 in a flow reactor under the following reaction conditions: temperature, 538° C. (propane and butane) and 625° C. (ethane); pressure, 1 atm.; GHSV, 170 hr⁻¹ (ethane), 700 hr⁻¹ (propane and isobutane), 530 hr$^{-1}$ (butane); and catalyst amount, 3 ml (sieved to pass 16 to 24 mesh).

The products were analyzed by a gas chromatograph connected to the reactor.

Table 16 shows the reaction results.

ancing the aluminum and gallium used for the synthesis was found in the crystalline aluminogallosilicates according to the present invention, it is implied that the aluminium and gallium are present in the crystal structure.

TABLE 16

| Catalyst | IV | | | | VIII | | | | IX |
|---|---|---|---|---|---|---|---|---|---|
| Feed | $C_3H_8$ | | $C_3H_8$ | | $i-C_4H_{10}$ | | $n-C_4H_{10}$ | | $C_2H_6$ |
| GHSV (hr$^{-1}$) | 700 | | 700 | | | | 530 | | 170 |
| Time of stream | | | | | | | | | |
| minutes | 30–70 | 70–130 | 30–70 | 70–130 | 27–67 | 69–129 | 28–68 | 70–130 | 40 |
| Convsn. % | 81.96 | 79.67 | 78.03 | 75.17 | 99.92 | 99.92 | 99.83 | 99.79 | 38.5 |
| Total effluent, % by weight | | | | | | | | | |
| $H_2$ | 5.20 | 4.96 | 5.43 | 5.11 | 5.09 | 4.92 | 5.22 | 5.12 | 4.01 |
| $C_1$ | 17.59 | 16.03 | 14.74 | 13.50 | 20.37 | 19.01 | 15.71 | 15.50 | 11.00 |
| $C_2$ | 5.85 | 5.46 | 5.19 | 5.04 | 4.32 | 4.18 | 6.34 | 6.45 | 61.47 |
| $C_3$ | 18.04 | 20.33 | 21.97 | 24.82 | 8.69 | 9.39 | 10.34 | 11.61 | 0.23 |
| $C_4$ | 0.42 | 0.48 | 0.53 | 0.60 | i 0.08 | i 0.08 | i 0.17 | i 0.10 | 0.00 |
| | | | | | n 0.14 | n 0.16 | n 0.08 | n 0.21 | |
| $C_2'-C_4'$ | 3.91 | 4.08 | 4.46 | 4.64 | 3.51 | 2.65 | 2.81 | 3.07 | 1.65 |
| $C_5^+$ | 0.03 | 0.04 | 0.06 | 0.05 | 0.00 | 0.00 | 0.00 | 0.00 | 0.00 |
| Benzene | 16.90 | 16.93 | 16.08 | 16.03 | 15.65 | 15.40 | 16.67 | 16.30 | 8.20 |
| Toluene | 19.32 | 19.31 | 18.84 | 18.40 | 25.14 | 25.34 | 24.68 | 24.37 | 3.89 |
| $C_8$ Arom | 6.16 | 6.54 | 6.45 | 6.33 | 10.37 | 10.99 | 9.58 | 9.72 | 0.49 |
| $C_9$ Arom | 1.05 | 1.08 | 1.08 | 1.09 | 1.49 | 1.70 | 1.45 | 1.51 | 0.25 |
| $C_{10}$ Arom | 2.59 | 2.26 | 2.49 | 2.14 | 2.65 | 2.61 | 2.99 | 2.64 | 4.58 |
| $C_{11}^+$ Arom | 2.94 | 2.49 | 2.68 | 2.28 | 3.50 | 3.57 | 3.96 | 3.40 | 4.23 |

EXAMPLE 30

Measurement of Acidity

Using the aluminosilicate (mole ratio of $SiO_2/Al_2O_3$:66) Al-4 and the gallosilicate Ga-3, prepared for comparative examples, and the aluminogallosilicate Al/Ga-10 as shown in Example 1 as samples, the ion exchange treatment was conducted using ammonium nitrate, thereby replacing a majority of the alkali metals contained in the samples. The samples were then dried and calcined at 550° C.

The thus calcined samples (each about 0.1 g) were heated at 400° C. for 3 hours under vacuo for deaeration. A degree of vacuum at this moment in each case was found to be $1 \times 10^{-4}$ torr or lower.

Using a multi-purpose calorimeter (manufactured by Tokyo Riko K. K.), each of the calcined samples was measured for heat of adsorption that generated when ammonia was added at the rate as small as $0.163 \pm 0.027$ cc per gram of the sample at 25° C. in the standard state at many times for adsorption. The measured results are shown in Table 17 below.

EXAMPLE 31

$^{29}$Si-MASNMR Measurement

The $^{29}$Si-MASNMR measurement was carried out using Model JNM-GX270 FTNMR (manufactured by Nippon Denshi K. K.) equipped with a solid CP/MAS unit (NM-GSH27HU). The measurement was conducted using the gated decoupling method under the following conditions: observed frequency, 53.67 MHz; data point, 8192; observed spectral width, 20,000 Hz; number of integration, 3,000–4,000; angle of pulse, 45' (5.3 μs); pulse repetition time, 5 seconds; and exterior standard substance, tetramethylsilane. Each of the measured $^{29}$Si-MASNMR spectra was subjected to waveform dissociation treatment and divided into Gauss type components.

It was measured from the $^{29}$Si-MASNMR spectra that, among the four tetrahedra ($TO_4$; T = Al, Ga or Si) adjacent to the ($SiO_4$) tetrahedron in the structure, both the tetrahedron in which T is occupied all by Si (represented by Si(0M)) and the tetrahedron in which only one o T's is occupied by Al or Ga (represented by

TABLE 17

| | Adsorption Quantity (mmol/g) | | |
|---|---|---|---|
| Heat of Adsorption (KJ/mol) | H-form Alumino-gallosilicate H-[Al/Ga-1] | H-form Alumino-silicate H-[Al-4] | H-form Gallo-silicate H-[Ga-3] |
| >150 | 0.10 | 0.02 | 0.06 |
| >130 | 0.15 | 0.06 | 0.09 |
| >100 | 0.47 | 0.20 | 0.27 |
| >80 | 0.70 | 0.37 | 0.40 |

As is apparent from the table above, the aluminogallosilicate according to the present invention is large with respect to the quantity of adsorption that generates the heat of adsorption equal to those of the aluminosilicate and the gallosilicate. As the degree of acidity bal- Si(1M)) were present. The mole ratios of $SiO_2$ to ($Al_2O_3 + Ga_2O_3$) were computed from the ratios of the spectral areas of Si(0M) to those of Si(1M). Table 18 below shows the results.

TABLE 18

| | Elemental Analysis | | | MASNMR |
|---|---|---|---|---|
| | $SiO_2/Ga_2O_3$ | $SiO_2/Al_2O_3$ | $SiO_2/(Ga_2O_3 + Al_2O_3)$ | $SiO_2/(Ga_2O_3 + Al_2O_3)$ |
| Aluminogallo- | 162.9 | 74.0 | 50.9 | 52 |

TABLE 18-continued

| | Elemental Analysis | | | MASNMR |
|---|---|---|---|---|
| | $SiO_2/Ga_2O_3$ | $SiO_2/Al_2O_3$ | $SiO_2/(Ga_2O_3 + Al_2O_3)$ | $SiO_2/(Ga_2O_3 + Al_2O_3)$ |
| silicate Al/Ga-10 | | | | |
| Aluminogallo-silicate Al/Ga-8 | 74.8 | 68.6 | 35.8 | 38 |

It is shown in Table 18 that the mole ratio of $SiO_2$ to $(Ga_2O_3+Al_2O_3)$ determined by the elemental analysis is virtually equal to that of the MASNMR and consequently that the aluminium and gallium are present in the crystal structure.

EXAMPLE 32

Preparation of Catalysts Carried with Metals

The extrudate (10 grams) of the $NH_4$-form aluminogallosilicate IX as shown in Table 4 was treated by getting it into contact with an aqueous solution of a metal salt in a manner as will be described below. The extrudate was dired at 120° C. for 3 hours in air and then calcined at 550° C. for 3 hours under air streams, thereby leading to the production of a final catalyst composition carried with the metal in the amount (as an elemental metal) as will be described below.

Na: The extrudate was immersed in a solution of 0.05 g of sodium nitrate in 11.6 ml of deionized water for one day at room temperature, filtered and washed with water. The amount of the metal carried was 0.12% by weight.

Mg: The same procedures as above were followed except that the immersion was conducted in a solution of 0.81 g of $Mg(NO_3)_2.6H_2O$ in 10 ml of deionized water. The metal amount was 0.30% by weight.

La: The same procedures as above were followed except that the extrudate was immersed in a solution of 0.91 g of $La(NO_3)_3.6H_2O$ in 10 ml of deionized water. The metal amount was 1.20% by weight.

V: The extrudate was immersed in a solution of 0.64 g of $NH_4VO_3$ in 40 ml of deionized water at 65° C. for 2 hours, filtered and washed with water. The metal amount was 0.90% by weight.

Cr: The extrudate was immersed in a solution of 4 g of $Cr(NO_3)_3.9H_2O$ in 50 ml of deionized water at room temperature for 7 days, filtered and washed with water. The metal amount was 0.45% by weight.

W: The extrudate was immersed in a solution of 1.13 g of $(NH_4)_{10}W_{12}O_{41}.5H_2O$ in 60 ml of deionized water at 60° C. for one day, filtered and washed with water. The metal amount was 3.05% by weight.

Mn: The same procedures as with Na were followed except for the immersion in a solution of 0.18 g of $Mn(NO_3)_2.6H_2O$ in 6.58 ml of deionized water. The metal amount was 0.36% by weight.

Re: The same procedures as with Na were followed except for the immersion in a solution of 0.17 g of $NH_4ReO_4$ in 6.58 ml of deionized water. The metal amount was 0.31% by weight.

Ir: The same procedures as with Na were followed except for the immersion in a solution of 0.21 g of $IrCl_3.1.5H_2O$ in 15 ml of deionized water for 2 days. The metal amount was 0.53% by weight.

Ni: The same procedures as with Na were followed except for the immersion in a solution of 7.27 g of $Ni(NO_3)_2.6H_2O$ in 50 ml of deionized water at 100° C. for 4 hours. The metal amount was 0.28% by weight.

Pt: The same procedures as with Na were followed except for the immersion in a solution of 0.08 g of $Pt(NH_3)_4Cl_2$ in 6.58 ml of deionized water. The metal amount was 0.42% by weight.

Zn: The same procedures as with Na were followed except for the immersion in a solution of 0.74 g of $Zn(NO_3)_2$ in 50 ml of deionized water for 4 hours. The metal amount was 0.35% by weight.

Sn: The same procedures as with Na were followed except for the immersion in a solution of 0.17 g of $SnC_2O_4$ in 10 ml of deionized water and 2 g of HCl. The metal amount was 0.74% by weight.

P: The same procedures as with Na were followed except for the immersion in a solution of 0.17 g of $NH_4HPO_4$ in 10 ml of deionized water for 7 days. The metal amount was 0.34% by weight.

Sb: The same procedures as with Na were followed except for the immersion in a solution of 10 g of toluene in 0.36 g of a toluene solution (25% as Sb) of Sb oxide. The metal amount was 0.47% by weight.

S: The same procedures as with Na were followed except for the immersion in a solution of 18.26 g of $(NH_4)_2S$ solution (0.5% as S). The metal amount was 0.04% by weight.

EXAMPLE 33

The aluminogallosilicate catalysts I, II, IV, V, VII and IX obtained in Example 2 were tested for their catalytic performace. Thus, using each catalyst, conversion of n-hexane was continuously performed for more than 25 hours under the following conditions:

| Raw Feed | n-Hexane |
|---|---|
| Reaction Temperature | 538° C. |
| Reaction Pressure | 1 atm. |
| LHSV | 2.0 $Hr^{-1}$ |

The conversion and aromatics yield were occasionally measured during the conversion operation. The results were as summarized in Table 19 and, by way of a graph, in FIG. 8.

Figure 8:
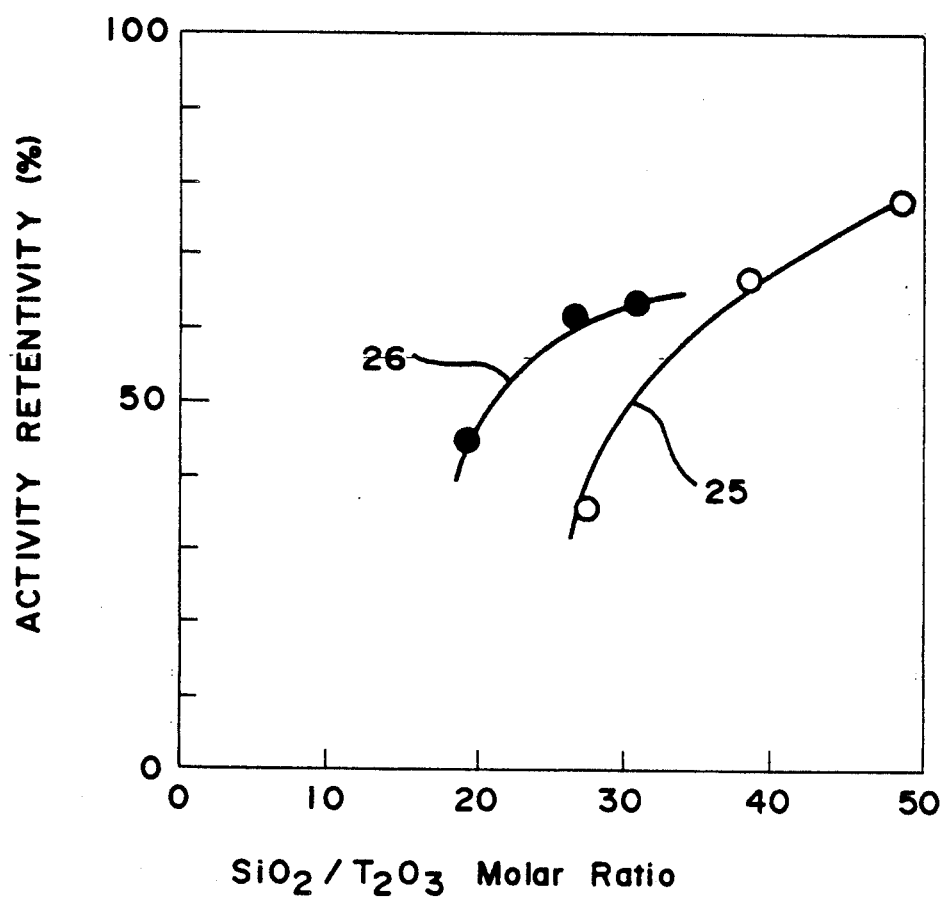

FIG. 8 is a graph showing the relationship between the $SiO_2/T_2O_3$ molar ratio and the activity retentivity of the aluminogallosilicate catalysts, in which Curve 26 is for aluminogallosilicate catalysts Nos. V, VII and IX having an aluminum content of about 1 wt % while Curve 27 is for aluminogallosilicate catalysts Nos. I, II and IV having an aluminum content of about 2 wt %. As seen from FIG. 8, a $SiO_2/T_2O_3$ molar ratio of at least 40 is required to provide an activity retentivity of about 70% or more.

TABLE 19

| Cat. No. | | Hours on Stream | | | | | | | | | Activity Retentivity* |
|---|---|---|---|---|---|---|---|---|---|---|---|
| | | 1 | 4 | 7 | 10 | 13 | 16 | 19 | 22 | 25 | |
| I | Conversion (%) | | 100 | 100 | 100 | 99.9 | 98.9 | 93.5 | 83.7 | 74.1 | 44.5 |
| | Aromatics Yield (wt %) | | 58.7 | 56.7 | 55.3 | 52.7 | 48.7 | 40.9 | 33.1 | 26.1 | |
| II | Conversion (%) | 100 | 100 | 100 | | | | | 99.6 | 98.6 | 60.9 |
| | Aromatics Yield (wt %) | 66.2 | 65.2 | 62.2 | | | | | 44.3 | 39.7 | |
| IV | Conversion (%) | 100 | 100 | 100 | 100 | 100 | 100 | 99.7 | 98.5 | 95.5 | 62.9 |
| | Aromatics Yield (wt %) | 63.6 | 62.3 | 60.0 | 57.4 | 55.1 | 52.8 | 49.1 | 44.4 | 39.2 | |
| V | Conversion (%) | 100 | 100 | 100 | 99.7 | 95.4 | | | | 63.7 | 34.9 |
| | Aromatics Yield (wt %) | 69.8 | 65.7 | 62.2 | 56.5 | 47.2 | | | | 22.9 | |
| VII | Conversion (%) | | 100 | 100 | 100 | 100 | 98.3 | 98.9 | 97.1 | 95.7 | 66.2 |
| | Aromatics Yield (wt %) | | 67.2 | 65.7 | 63.2 | 59.7 | 56.1 | 51.3 | 46.9 | 44.5 | |
| IX | Conversion (%) | 100 | 100 | 100 | 100 | 100 | | 99.9 | 99.6 | 98.7 | 76.7 |
| | Aromatics Yield (wt %) | 67.6 | 67.3 | 65.8 | 63.8 | 62.2 | | 60.9 | 55.3 | 51.6 | |

*Activity Retentivity = $\dfrac{\text{Aromatics yield at 25 hour-process time}}{\text{Aromatics at 4 hour-process time}} \times 100(\%)$

We claim:

1. A crystalline aluminogallosilicate having the skeleton comprised of $SiO_4$, $AlO_4$ and $GaO_4$ tetrahedra, having an MFI structure and having the following formula:

$$aM_{2/n}O \cdot bAl_2O_3 \cdot Ga_2O_3 \cdot cSiO_2 \cdot dH_2O$$

wherein M is a metal selected from an alkali metal, an alkaline earth metal and a mixture thereof, n is the valence of said metal, a is a positive number of $(b+1)\pm 3.0$, b is between 1 and 6, c is between 80 and 490, d is between 1 and 200, $c/(b+1)$ is between 45 and 65, and $c/b$ is between 46.7–140.

2. The aluminogallosilicate of claim 1 wherein $c/(b+1)$ is 45–60.

UNITED STATES PATENT AND TRADEMARK OFFICE
CERTIFICATE OF CORRECTION

PATENT NO. : 4,994,254

DATED : February 19, 1991

INVENTOR(S) : SUZUKI et al

It is certified that error appears in the above-identified patent and that said Letters Patent is hereby corrected as shown below:

On the title page item [75] under the heading "Inventors" add the following: --Tadami Kondoh and Hiroaki Nishijima, both of Ebina, Japan--

Column 3, line 25, "slat" should read --salt--.

Column 20, line 48, "o" should read --of--.

Signed and Sealed this

First Day of December, 1992

Attest:

DOUGLAS B. COMER

*Attesting Officer*    *Acting Commissioner of Patents and Trademarks*